United States Patent [19]

Eicken et al.

[11] 4,376,645

[45] Mar. 15, 1983

[54] 2'-PHENYLHYDRAZINO-2-CYANOACRYLIC ACID ESTERS AND HERBICIDES CONTAINING THESE COMPOUNDS

[75] Inventors: Karl Eicken, Wachenheim; Peter Plath, Ludwigshafen; Bruno Wuerzer, Otterstadt, all of Fed. Rep. of Germany

[73] Assignee: BASF Aktiengesellschaft, Fed. Rep. of Germany

[21] Appl. No.: 322,674

[22] Filed: Nov. 18, 1981

[30] Foreign Application Priority Data

Dec. 5, 1980 [DE] Fed. Rep. of Germany ....... 3045903
Jul. 4, 1981 [DE] Fed. Rep. of Germany ....... 3126479

[51] Int. Cl.³ .................... A01N 37/34; C07C 121/78
[52] U.S. Cl. .................................. 71/105; 260/465 D
[58] Field of Search ...................... 260/465 D; 71/105

[56] References Cited

U.S. PATENT DOCUMENTS 2,792,296  5/1957  Heininger ................... 71/105 X
3,062,635  11/1962 Acker et al. ................ 71/105 X
3,726,662  4/1973  Howe et al. ................ 71/105 X

OTHER PUBLICATIONS

Farmaco Ed. Sci. 22 (1967), pp. 58–75 and p. 418.

*Primary Examiner*—Dolph H. Torrence
*Attorney, Agent, or Firm*—Keil & Witherspoon

[57] ABSTRACT

2'-Phenylhydrazino-2-cyanoacrylic acid esters of the formula

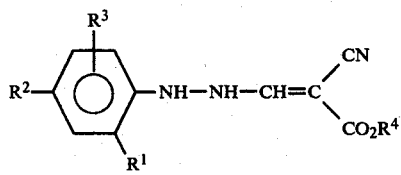

wherein $R^1$ is methyl, trifluoromethyl, chlorine or bromine, $R^2$ is chlorine, bromine, iodine or methylsulfonyl, $R^3$ is hydrogen, chlorine or bromine, or methoxy in the 5-position, in which case $R^1$ and $R^2$ are chlorine, or $R^3$ is chlorine in the 3-position, in which case $R^2$ is hydrogen, and $R^4$ is alkyl of 1 to 3 carbon atoms, allyl or propargyl, and herbicides containing these compounds.

6 Claims, No Drawings

2'-PHENYLHYDRAZINO-2-CYANOACRYLIC ACID ESTERS AND HERBICIDES CONTAINING THESE COMPOUNDS

The present invention relates to 2'-phenylhydrazino-2-cyanoacrylic acid esters and herbicides which contain these compounds.

2'-Phenylhydrazino-2-cyanoacrylic acid esters which have a chlorine atom or nitro group in the phenyl radical have been disclosed in the literature (Farmaco Ed. Sci. 22 (1967), 58; 418). They are used as intermediates, eg. for the synthesis of diuretics or antibacterial compounds. No herbicidal properties have been disclosed for these compounds.

We have found that 2'-phenylhydrazino-2-cyanoacrylic acid esters of the formula I

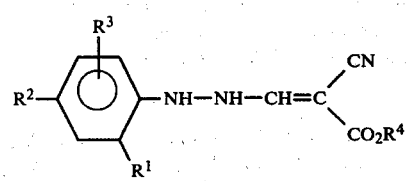

where $R^1$ is methyl, trifluoromethyl, chlorine or bromine, $R^2$ is chlorine, bromine, iodine or methylsulfonyl, $R^3$ is hydrogen, chlorine or bromine, or methoxy in the 5-position, in which case $R^1$ and $R^2$ are chlorine, or $R^3$ is chlorine in the 3-position, in which case $R^2$ is hydrogen, and $R^4$ is alkyl of 1 to 3 carbon atoms, allyl or propargyl, have a surprisingly powerful and at the same time selective herbicidal action.

The 2'-phenylhydrazino-2-cyanoacrylic acid esters of the formula I are obtained, for example, by reacting a substituted phenylhydrazine of the formula II

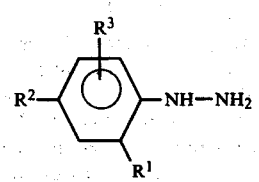

where $R^1$, $R^2$ and $R^3$ have the above meanings, with a substituted 2-cyanoacrylic acid ester of the formula III

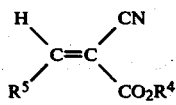

where $R^4$ has the above meanings and $R^5$ is alkoxy of 1 to 4 carbon atoms, N,N-dialkylamino, where alkyl is of 1 to 4 carbon atoms, or hydroxyl.

The reaction is advantageously carried out under mild conditions, at from −25° to 70° C., preferably at room temperature (20° C.).

Suitable solvents are those in which both reactants are soluble or partly soluble, especially alcohols, such as methanol, ethanol, propanol, i-propanol and butanol, ethers, such as tetrahydrofuran and dioxane, and mixtures of these solvents.

The 2'-phenylhydrazino-2-cyanoacrylic acid esters of the formula I according to the invention in most cases crystallize out of the reaction solution in a pure form, and can be isolated by filtration with suction and drying under mild conditions (below 50° C.).

Not less than the molar amount, based on the substituted phenylhydrazines of the formula II, and preferably the stoichiometric amount, of the 2-cyanoacrylic acid esters of the formula III is used. If, instead of the free phenylhydrazines of the formula II, mineral acid salts are used, eg. hydrochlorides or sulfates, it is advantageous first to liberate the substituted phenylhydrazine of the formula II by adding an equivalent amount of an alkali metal alcoholate or alkali metal acetate and then to carry out the reaction.

Those phenylhydrazines of the formula II which are not already known can be prepared by a conventional method (Houben-Weyl, Methoden der Organ. Chemie, volume 10/2, page 180 et seq.). Those 2-cyanoacrylic acid esters of the formula III which are not already known can be prepared by a conventional method (German Laid-Open Application DOS No. 2,635,841; Chem. Ber. 97 (1964), 3397).

In the Examples which follow, parts by weight bear the same relation to parts by volume as that of the kilogram to the liter.

Preparation of the 2'-phenylhydrazino-2-cyanoacrylic acid esters of the formula I

EXAMPLE 1

148.1 parts by weight of 2,4,6-trichlorophenylhydrazine are introduced into a solution of 108.5 parts by weight of methyl ethoxymethylene-2-cyanoacetate in 1,000 parts by volume of methanol. A crystal slurry precipitates out of the solution and is stirred for 3 hours and filtered with suction, and the crystals are dried at 40° C. under reduced pressure to give 187.4 parts by weight of methyl 2'-(2,4,6-trichlorophenyl)-hydrazino-2-cyanoacrylate of melting point 174°–175° C. (Compound No. 1).

$C_{11}H_8Cl_3N_3O_2$ (Molecular weight 320.5) Calculated: C, 41.22; H, 2.25; N, 13.11. Found: C, 40.9; H, 2.8; N, 12.8.

EXAMPLE 2

A suspension of 21.4 parts by weight of 2,4-dichlorophenylhydrazine hydrochloride in 150 parts by volume of methanol is neutralized by adding about 18 parts by weight of 30% strength sodium ethylate solution, and, after addition of 15.5 parts by weight of methyl ethoxymethylene-2-cyanoacetate, the mixture is stirred at 25° C. for 3 hours and refluxed for 15 minutes. It is then filtered, the methanol is evaporated from the filtrate under reduced pressure and the residue is recrystallized from ethanol (at 50° C.) to give 17.5 parts by weight of methyl 2'-(2,4-dichlorophenyl)-hydrazino-2-cyanoacrylate of melting point 154°–156° C. (Compound No. 2).

$C_{11}H_9Cl_2N_3O_2$ (Molecular weight 286) Calculated: C, 46.18; H, 3.17; N, 14.69. Found: C, 46.0; H, 3.2; N, 14.8.

The following 2'phenylhydrazino-2-cyanoacrylic acid esters of the formula I can be prepared in a corresponding manner:

| No. | $R^1$ | $R^2$ | $R^3$ | $R^4$ | Melting point (°C.) |
|---|---|---|---|---|---|
| 3 | Cl | Cl | H | $C_2H_5$ | 175 |
| 4 | Cl | Cl | 6-Cl | $C_2H_5$ | 166 |
| 5 | Cl | Cl | 6-Cl | $i\text{-}C_3H_7$ | 130 |

-continued

| No. | $R^1$ | $R^2$ | $R^3$ | $R^4$ | Melting point (°C.) |
|---|---|---|---|---|---|
| 6 | $CH_3$ | Cl | H | $CH_3$ | 140 |
| 7 | Br | Br | 6-Br | $CH_3$ | 182 |
| 8 | Cl | Br | 5-Cl | $CH_3$ | |
| 9 | Cl | Cl | 5-Cl | $CH_3$ | 195 |
| 10 | $CH_3$ | Br | H | $CH_3$ | |
| 11 | $CH_3$ | Br | 6-Br | $CH_3$ | |
| 12 | $CH_3$ | Cl | 6-Cl | $CH_3$ | |
| 13 | Cl | Cl | 6-Br | $CH_3$ | |
| 14 | Cl | Br | 6-Br | $CH_3$ | |
| 15 | Cl | Br | 6-Cl | $CH_3$ | |
| 16 | Br | Cl | 6-Br | $CH_3$ | |
| 17 | Br | Br | H | $CH_3$ | |
| 18 | Cl | Cl | 5-$CH_3O$ | $CH_3$ | |
| 19 | Cl | Cl | 6-Cl | $CH_2CH=CH_2$ | 156 |
| 20 | Cl | $SO_2CH_3$ | H | $CH_3$ | |
| 21 | Cl | Cl | 6-Cl | Propargyl | |
| 22 | Cl | H | 3-Cl | $CH_3$ | |

Application as herbicide may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

The herbicides contain, for example, from 5 to 95, especially 10 to 80, wt% of active ingredient.

Examples of surfactants are: alkali metal, alkaline earth metal and ammonium salts of ligninsulfonic acid, napthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalene-sulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

EXAMPLE A 90 parts by weight of compound 1 is mixed with 10 parts by weight of N-methyl-α-pyrrolidone. A mixture is obtained which is suitable for application in the form of very fine drops.

EXAMPLE B 10 parts by weight of compound 2 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

EXAMPLE C 20 parts by weight of compound 2 is dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

EXAMPLE D 20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil.

EXAMPLE E 80 parts by weight of compound 1 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill.

EXAMPLE F 5 parts by weight of compound 2 is intimately mixed with 95 parts by weight of particulate kaolin. A dust is obtained containing 5% by weight of the active ingredient.

EXAMPLE G 30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE H 40 parts by weight of compound 2 is intimately mixed with 10 parts of the sodium salt of a phenolsulfonic acid-urea-formaldehyde condensate, 2 parts of silica gel and 48 parts of water. Dilution in water gives an aqueous dispersion.

EXAMPLE I 20 parts of compound 1 is intimately mixed with 12 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The influence of various representatives of the novel 2'-phenylhydrazino-2-cyanoacrylic acid esters on the growth of unwanted plants is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species.

In the preemergence treatment, the active ingredients were applied to the surface of the soil as a suspension or emulsion in water by spraying through finely distributing nozzles. The amount of active ingredient applied in this treatment was equivalent to 3.0 kg/ha.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 10 cm, depending on growth form, before being treated. For this treatment, either plants which had been sown directly in the pots and grown there were selected, or plants which had been grown separately as seedlings and transplanted to the experiment vessels a few days before treatment. Where rice was used for the postemergence treatment, the substrate was enriched with peat. The same is true of catchweed bedstraw. The amount of active ingredient applied in this treatment was 0.5 kg/ha for novel compound no. 1 and 3.0 kg/ha for compounds nos. 1 and 2. No cover was placed on the vessels in this treatment.

The pots were set up in the greenhouse—species from warmer areas at from 20° to 35° C., and species from moderate climates at 15° to 25° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The greenhouse experiments show that compound nos. 1 and 2, on both pre- and postemergence application at 3.0 kg/ha, have a good herbicidal action.

In these greenhouse experiments, compound no. 1 also has, at 0.5 kg/ha, a very good action on a whole range of unwanted plants. Certain crop plants tolerate treatment with this active ingredient with slight and temporary damage, if any at all.

If certain crop plants tolerate, on leaf treatment, the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

In view of the many application methods possible, the herbicides according to the invention may be used in a very wide range of crops for removing unwanted plants. The application rates may vary between 0.1 and 15 kg of active ingredient per hectare and more.

To increase the spectrum of action and to achieve synergistic effects, the novel compounds according to the invention may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

TABLE 1

| List of plant names | |
|---|---|
| Botanical name | Common name |
| Abutilon theophrasti | velvet leaf |
| Amaranthus spp. | pigweed |
| Centaurea cyanus | cornflower |
| Daucus carota | wild carrot |
| Galium aparine | catchweed bedstraw |
| Ipomoea spp. | morningglory |
| Lamium purpureum | henbit |
| Oryza sativa | rice |
| Sida spinosa | teaweed (prickly sida) |
| Sinapis alba | white mustard |
| Solanum nigrum | black nightshade |
| Tricitum aestivum | wheat |

We claim:

1. A 2'-phenylhydrazino-2-cyanoacrylic acid ester of the formula

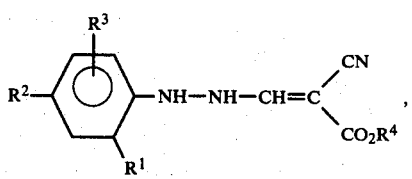

where $R^1$ is chlorine or bromine, $R^2$ is chlorine, bromine or iodine, $R^3$ is chlorine or bromine, and $R^4$ is alkyl of 1 to 3 carbon atoms, allyl or propargyl.

2. Methyl 2'-(2,4,6-trichlorophenyl)-hydrazino-2-cyanoacrylate.

3. A compound of the formula I as described in claim 1 wherein $R^4$ is methyl.

4. A process for combating unwanted plants, wherein the plants or the soil are treated with a 2'-phenylhydrazino-2-cyanoacrylic acid ester of the formula

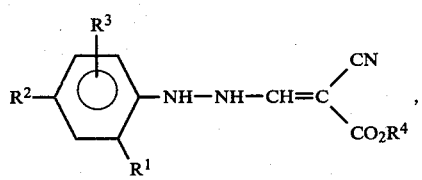

where $R^1$ is methyl, trifluoromethyl, chlorine or bromine, $R^2$ is chlorine, bromine, iodine or methylsulfonyl, $R^3$ is hydrogen, chlorine or bromine, or methoxy in the 5-position, in which case $R^1$ and $R^2$ are chlorine, or $R^3$ is chlorine in the 3-position, in which case $R^2$ is hydrogen, and $R^4$ is alkyl of 1 to 3 carbon atoms, allyl or propargyl.

5. A herbicidal composition comprising a carrier or diluent and a herbicidally effective amount of a compound of the formula I

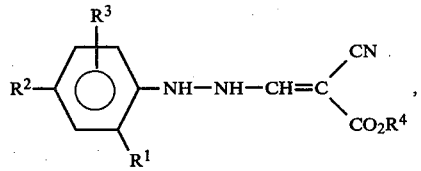

where $R^1$ is methyl, trifluoromethyl, chlorine or bromine, $R^2$ is chlorine, bromine, iodine or methylsulfonyl, $R^3$ is hydrogen, chlorine or bromine, or methoxy in the 5-position, in which case $R^1$ and $R^2$ are chlorine, or $R^3$ is chlorine in the 3-position, in which case $R^2$ is hydrogen, and $R^4$ is alkyl of 1 to 3 carbon atoms.

6. A herbicidal composition comprising a carrier or diluent and a herbicidally effective amount of a compound of the formula I as described in claim 3.

* * * * *